US00PP10670P

United States Patent [19]

Larsen

[11] Patent Number: Plant 10,670

[45] Date of Patent: Nov. 3, 1998

[54] OSTEOSPERMUM PLANT NAMED 'SUNNY GUSTAF'

[75] Inventor: Bjarne Larsen, Odense, Denmark

[73] Assignee: Paul Ecke Ranch, Encinitas, Calif.

[21] Appl. No.: 698,340

[22] Filed: Aug. 15, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV–ROM Plant Variety Database 'Sunny Gustaf', Osteospermum, PBR OST 96/055, 1996.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Sunny Gustaf', particularly characterized by its spreading growth habit and white flower color, medium season flower timing and medium green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Sunny Gustaf', and was developed by the inventor Bjarne Larsen in Odense, Denmark in 1991 by crossing the unpatented cultivar designated 'Sunny Boy' with the unpatented cultivar 'Whirlygig'.

Asexual reproduction by terminal (stem tip) cuttings taken by me or under my supervision at Kernen Greenhouse in Odense, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique floriferous white flower with a blue eye.
2. A spreading compact growth habit.
3. Medium timing flower response.
4. Well suited for 6" pots, nursery containers, and hanging baskets.

'Sunny Gustaf' is similar to 'Sunny Boy'. The growth habit of 'Sunny Gustaf' is more spreading, flower petioles are shorter, and plant flower size is smaller.

Chart A shows a comparison of 'Sunny Gustaf' with 'Cape Daisy Nairobi', a plant described and illustrated in co-pending U.S. patent application Ser. No. 08/698,341 which is the most comparable plant to the knowledge of the inventor. The plants described in Chart A include 3 plants grown in one hanging basket.

CHART A

| Characteristic | 'Sunny Gustaf' | 'Cape Daisy Nairobi' |
|---|---|---|
| Plant Height (above the pot) | 32 cm | 28 cm |
| Plant Width | 60 cm | 50 cm |
| Flower Head Diameter | 6.2 cm | 7.7 cm |

DESCRIPTION OF PHOTOGRAPH

The accompanying colored photograph is a side perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif., Three rooted cuttings were transplanted into 26 cm (10 inch) hanging baskets on Dec. 11, 1995. Plants were pinched on Jan. 2, 1996, and received plant growth regulator on January 16 and 31. The values, measurements and observations noted below were taken from plants in bloom on Feb. 29, 1996, and continued in flower through April 1996.

On Apr. 10, 1996, I observed a plant in a 26 cm hanging basket 32 cm tall. This basket had three branched plants with an overall height of 47.5 cm and an overall width of 60 cm. Each plant had 6 strong branches, originating from within 1.5 cm of the soil line, for a total of 18 branches. Each branch was approximately 29 cm long terminating in a flower. At observation, there were 92 flowers open and 156 flower buds in various stages of development. Three secondary shoots subtend the terminal flower from the top 3 nodes on the primary shoot. These secondary shoots also terminated in a flower.

Color references are made to The Royal Horticultural Society Colour Chart (R.H.S.), except where general terms of ordinary dictionary signifcance are used.

The Plant

Origin: Seedling from cross pollination.

Parentage: Cross between Seed Parent 'Sunny Boy' and Pollen Parent 'Whirlygig'.

Classification:

*Botanical.*—*Osteosperumum ecklonis.*

*Common name.*—Osteosperum.

*Cultivar name.*—'Sunny Gustaf'.

Asexual Reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitous roots from the stem base.

D. *Growth retardant application.*—Standard growth retardant application for 'Sunny Gustaf' includes 1–2 applications of daminozide/butanedioic acid mono (2.2 dimethylhydrazide) at a rate of 2,500 ppm. Applications are made as foliar sprays. Growth retarding chemicals generally reduce plant height ⅓.

Plant description:

A. *Form.*—Symmetrical, low growing perennial shrub, with good branching characteristics after pinching, giving the plant a full appearance.

B. *Habit of growth.*—Vigorous, spreading habit, producing approximately 14 leaves per stem and terminating in flowers. After the initial flower is formed, typically 3 subordinate axillary shoots develop from the uppermost leaves producing additional flowering shoots. This process is continuous so long as night temperatures remain below 16° C.

*Foliage description.*—1. Leaf shape: Obovate with acuminate tip and attenuate leaf base. 2. Leaf blade size: Mature leaves 6–8 cm long and 3 cm wide. 3. Petiole length: Approximately 1.5 to 2 cm in length. 4. Leaf Margin: Slightly sinuate with 3 to 5 points lobes on either side of the leaf blade. 5. Leaf texture: Slightly undulant and twisted at the tip. i) Upper surface: Slightly pubescent with short, white trichomes evenly distributed throughout the leaf surface. ii) Under surface: Slightly pubescent with short trichomes. 6. Leaf color: Dark green. i) Upper surface: Near R.H.S. 147A. ii) Under surface: Lighter than R.H.S. 147A. 7. Venation: Palmately branched with one light green colored mid-vein predominately on the upper surface. One predominate mid-vein is slightly raised on the lower surface. 8. Foliage fragrance: Characteristic Osteospermum plant fragrance, particularly notable when foliage is wet.

Inflorescence description: Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

A. *Flowering habits.*—Flowering is determinate with one primary flower at the end of a long 13–19 cm pedicel on open flowers. Each pedicel had approximately 4–5 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates. Plants are initially potted using rooted cuttings, pinched 2 weeks later, then maintained at a temperature of 10°–12° C. for 4 weeks and thereafter grown for 9 weeks at a temperature of 18° C., for a total growing time to flower of 15 weeks.

C. *Flower buds.*—Flower buds develop successively on secondary branches, reaching a size of 1.8 cm long and 1 cm wide prior to opening.

D. *Flowers borne.*—Singularly 5 cm above the plant canopy.

E. *Quantity of flowers.*—Secondary flowers occur progressively around the primary flower so that tight buds to mature flowers are visible at the same time.

F. *Flower head.*—1. Number of florets: 15–16 ray florets and numerous disk florets, making up a flower disk approximately 1 cm in diameter. 2. Shape: Narrow linear florets with obtuse to acute tips and acute bases. Ray florets are approximately 2.7 cm long and 0.9 cm wide. 3. Color: Ray florets are white; disk florets are blue. (i) Upper surface of ray florets: Pure white, not as yellow as R.H.S. 155C. (ii) Under surface of ray petals: Violet alternating longitudinal strips near R.H.S. 77D and 85D. (iii) Disk florets: Near R.H.S. 96A. 4. Surface: (i) Upper surface of ray florets: Gladbrous. (ii) Under surface of ray florets: Glabrous but pubescent near the base. 5. Inflorescence size: Up to 6.2 cm in diameter. 6. Flower fragrance: None.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2 mm long and purple. 6. Ovary: Inferior to florets and green in color.

H. *Resistance.*—1. Frost: Withstands light frost. 2. Diseases: Resistant to most root, stem, foliage and flower diseases.

What is claimed is:

1. A new and distinct cultivar of Osteospermum plant named 'Sunny Gustaf' as illustrated and described.

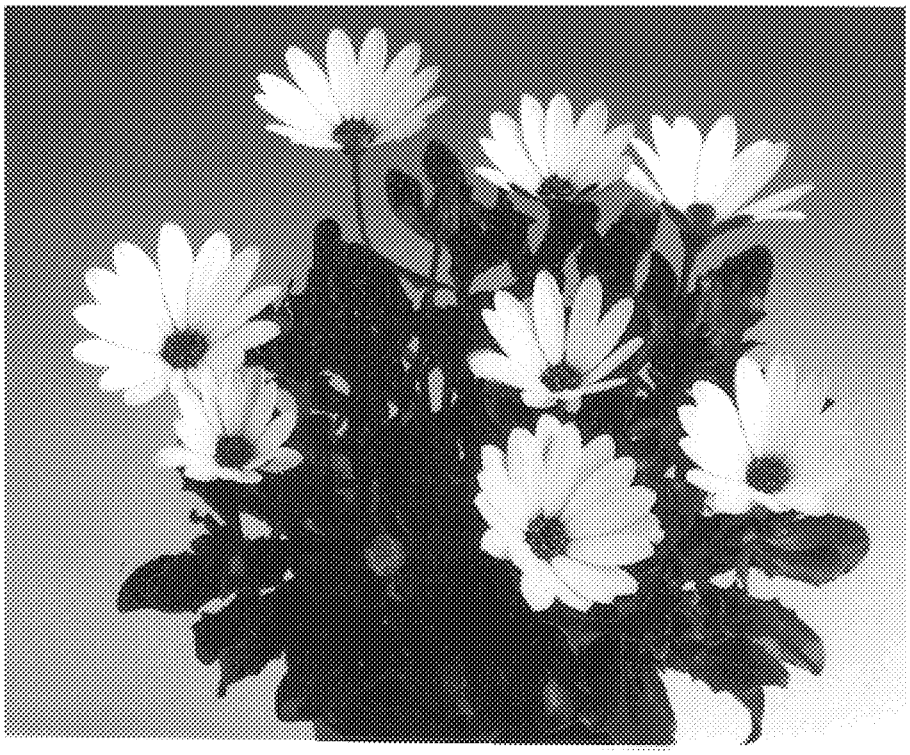

* * * * *